US005488042A

United States Patent [19]
Grdina

[11] Patent Number: 5,488,042
[45] Date of Patent: Jan. 30, 1996

[54] METHOD FOR PROTECTION AGAINST GENOTOXIC MUTAGENESIS

[75] Inventor: David J. Grdina, Naperville, Ill.

[73] Assignee: Arch Development Corporation, Chicago, Ill.

[21] Appl. No.: 851,210

[22] Filed: Mar. 13, 1992

[51] Int. Cl.$^6$ .................................................. A61K 31/66
[52] U.S. Cl. .............................. 514/114; 511/43; 511/555; 511/665
[58] Field of Search .................................. 514/114, 555, 514/665, 43

[56] References Cited

U.S. PATENT DOCUMENTS

| 3,842,824 | 7/1975 | Piper | 564/166 |
|---|---|---|---|
| 5,217,964 | 6/1993 | Edwards | 514/104 |

OTHER PUBLICATIONS

Smoluk, Cancer Research, 48 3641 (1985).
Livesy, Biochemical Pharmacology, 39 1807 (1990).
Sweeney, R. T., "A Survey of Compounds From the Anti-radiation Drug Development Program of the U.S. Army Medical Research and Development Command," Walter Reed Army Institute of Research, Washington, D.C., Sep. 1979.
Corn, B. W., Liber, H. L. and Little, J. B., "Differential Effects of Radical Scavengers on X-Ray-Induced Mutation and Cytotoxicity in Human Cells," *Radiation Research* 109, 100–108 (1987).
Nygaard, O. F. and Simic, M. G., excerpt from *Radioprotectors and Anticarcinogens*, 73–85, (1983).
Grdina, D. J., Dale, P. and Weichselbaum, R., "Protection Against AZT-Induced Mutagenesis at the HGPRT Locus in Human Cell Line by WR-151326," submitted for publication in Jan. 1991 to *The International Journal of Radiation Oncology, Biology, Physics*; presented at the Seventh International Conference on Chemical Modifiers of Cancer Treatment, Clearwater, Florida, Feb. 2–5, 1991.
Milas, L., Hunter, N. and Stephens, L. C. and Peters, L. J., "Inhibition of Radiation Carcinogenesis in Mice by S–2(3–Aminopropylamino)–Methylphosphorothioic Acid," *Cancer Research*, vol. 44, 5567–5569, Dec. 1984.
Grdina, D. J., Carnes, B. A., Grahn, D. and Sigdestad, C. P. "Protection Against Radiation–Induced Late Effects S–2–(3–Aminopropylamino)–Ethylphosphorothioic Acid," submitted to *Cancer Research* for publication, Jan. 1991.
Brown, J. M., "Sensitizers and Protectors in Radiotherapy," *Cancer*, 2222–2228, May 1 Supplement, 1985.
Constine, L. S., Zagars, G., Rubin, P. and Kligerman, M., "Protection by WR-2721 of Human Bone Marrow Function Following Irradiation," *Int. J. Radiation Oncology Biol. Phys.*, vol. 12, 1505–1508, (1986).
Mahoney, F., "Summary Statement," Radiation Study Section, Feb. 1986.
Grdina, D. J., Nagy, B., Hill, C. K. and Sigdestad, C. P., "Protection Against Radiation–Induced Mutagenesis in V79 Cells by 2–[(Aminoprophyl) amino] Ethanethiol Under Conditions of Acute Hypoxia," *Radiation Research* vol. 117, 251–258 (1989).
"Summary Statement," Radiation Study Section, Jan. 1989.
Maisin, J. R., Mattelin, G. and Lambiet–Collier, M., "Chemical Protection against the Long–Term Effects of a Single Whole–Body Exposure of Mice to Ionizing Radiation," *Radiation Research* 71, 119–131 (1977).
Kataoka, R., Basic, I., Perrin, J. and Grdina, D. J., "Anti–mutagenic effects of radioprotector WR–2721 against fission–spectrum–neutrons and Co–gamma rays in mice," submitted to *Int. J. Radiation Oncology Biol. Phys.* for publication in Mar. 1991.
Fry, R. J. M., "Radiation Carcinogenesis: Radioprotectors and Photosensitizers," *Radioprotectors and Anticarcinogens*, 417–436, (1983).
Held, K. D., "Models for Thiol Protection of DNA in Cells," *Pharmac. Ther.*, vol. 39, 123–131, (1988).
Grdina, D. J. and Sigdestad, C. P., "Radiation Protectors: The Unexpected Benefits," *Drug Metabolism Reviews*, 20(1), 13–42, (1989).
"1990 AACR Abstract Form," Temporary Abst. No. 247, of the paper Antimutagenic and Anticarcinogenic Effects of Aminothiols: Applications to the Clinic and Workplace.
"Abstracts," 3rd International Conference on Anticarcinogenesis & Radiation Protection, Oct. 15–21, 1989.
"Abstracts," Twenty–Eighth Plenary Meeting of the Committee on Space Research, Jun. 25–Jul. 6, 1990.
Kataoka, Y., Basic, I., Perrin J. and Grdina, D. J., "Antimutagenic effects of radioprotector WR–2721 against fission–spectrum neutrons $^{60}$Co gamma–rays in mice,"*Int. J. Radiat. Biol.*, (1992).
Zhang, X., Lai, P. and Taylor, Y., "Differential Radioprotection of Cultured Human Diploid Fibroblasts and Fibrosarcoma Cells by WR1065," *International Journal of Radiation Oncology, Biology, Physics*, vol. 21, Supp. 1, (1991).
Grdina, D. J., Kataoka, Y., Basic, I. and Perrin, J., "The radioprotector WR–2721 reduces neutron–induced mutations at the hypoxathine–guanine phosphoribosyl transferase locus in mouse splenocytes when administered prior to or following irradiation," submitted to *Carcinogenesis* for publication in 1991.
Grdina, D. J., Carnes, B. A., Grahn, D. and Sigdestad, C. P., "Protection against Late Effects of Radiation by S–2–(3–Aminopropylamino)–ethylphosphorothioic Acid," *Cancer Research* vol. 51, 4125–4130, Aug. 15, 1991.
Carnes, B. A. and Grdina, D. J., "In vivo protection by the aminothiol WR–2721 against neutron–induced carinogenesis," submitted to *Int. J. Radiat. Biol.* for publication in 1991.

(List continued on next page.)

*Primary Examiner*—Robert Gerstl
*Attorney, Agent, or Firm*—Reinhart, Boerner, Van Deuren, Norris & Rieselbach

[57] ABSTRACT

A method and pharmaceutical for protecting against genotoxic damage in irradiated cells. Reduction of mutations at the hypoxanthine-guanine phosphoribosyl transferase locus is accomplished by administering an effective dose of a compound having protected sulfhydryl groups which metabolize in vivo to produce both free sulfhydryl groups and disulfides.

4 Claims, 10 Drawing Sheets

OTHER PUBLICATIONS

Grdina, D. J., Wright, B. J. and Carnes, B. A., "Protection by WR–151327 against Late–Effect Damage from Fission–Spectrum Neutrons," *Radiation Research* 127, (1991).

Kataoka, Y., Perrin, J. and Grdina, D. J., "Protection by WR2721 Against Fission–Neutron–Induced Mutagenesis in Mice".

Kataoka, Y., Basic, I., Perrin, J. and Grdina, D. J., "Anti–mutagenic effects of radioprotector WR–2721 against fission–spectrum–neutrons and $^{60}$Co gamma–rays in mice," *Int. J. Radiat. Biol.*, (1991).

Smoluik, G. D., Fahey, R. C., Calabro–Jones, P. M. Aguilera, J. A. and Ward, J. F., "Radioprotection of Cells in Culture by WR–2721 and Derivatives: Form of the Drug Responsible for Protection," *Cancer Research* vol. 48, 3641–3647, Jul. 1, 1988.

Holwitt, E. A., Koda, E. and Swenberg, C. E., "Enhancement of Topoisomerase I–Mediated Unwinding of Supercoiled DNA by the Radioprotector WR–33278," *Radiation Research* 124, 107–109, (1990).

Grdina and Sigdestad, "Exhibit 1," (FIG. 1–Radiation Inactivation of Mamalian Cells).

Benova, D., "Antimutagenic Properties of WR 2721 and of a Radioprotective Mixture, ATP–AET–Serotonin, With Regard to X–Ray Induced Reciprocal Translocations in Mouse Spermatogonia," *Int. J. Radiation Oncology Biol. Phys.*, vol. 13, 117–119 (1987).

$H_2N-(CH_2)_3-NH-(CH_2)_2-\boxed{S-S}-(CH_2)_2-NH-(CH_2)_3-NH_2$

WR-33278

$H_2N-(CH_2)_3-NH-(CH_2)_2-(CH_2)_2-NH-(CH_2)_3-NH_2$

SPERMINE

FIGURE 6

3-[(2-mercaptoethyl) amino] propionamide p-toluenesulfonate (WR-2529)

$$N_2NCCH_2\ NH\ CH_2\ CH_2-SH\ (CH_3\ O\ SO_3H)$$
with O double-bonded to the C of NCCH$_2$ S-1-(2-hydroxy-3-amino) propyl phosphorothioic acid (WR-77913)
$$N_2N\ CH_2\ CH\ (OH)\ CH_2\ SPO_3\ H_2$$

2-[3-(methylamino) propylamino] ethanethiol (WR-255591)
$$CH_3\ NH(CH_2)_3\ NH\ CH_2\ CH_2\ SH$$

S-1-(aminoethyl) phosphorothioic acid (WR-638)
$$H_2N\ CH_2\ CH_2\ SPO_3\ H_2$$

S-[2-(3-methylaminopropyl) aminoethyl] phosphorothioate acid (WR-3689)
$$CH_3NH\ (CH_2)_3\ NHCH_2\ CH_2\ SPO_3\ H_2$$

S-2-(4-aminobutylamino) ethylphosphorothioic acid (WR-2822)
$$H_2N\ (CH_2)_4\ NH\ CH_2\ CH_2\ CH_2\ SPO_3\ H_2$$

FIG. 7A

S-2-(5-aminopentylamino) ethyl phosphorothioic acid     (WR-2823)

$H_2N(CH_2)_5 NH\ CH_2\ CH_2\ SPO_3\ H_2$

1-[3-(3-aminopropyl) thiazolidin-2-Yl]-D-gluco-1,2,3,4,5-     (WR-255709)
pentane-pentol dehydrochloride S-2-(3-aminopropylamino) ethylphosphorothioic acid     (WR-2721)

$NH_2(CH_2)_3\ NH\ CH_2\ CH_2\ S\ PO_3\ H_2$

2-[(aminopropyl) amino] ethanethiol     (WR-1065)

$NH_2(CH_2)_3\ NH\ CH_2\ CH_2\ SH$

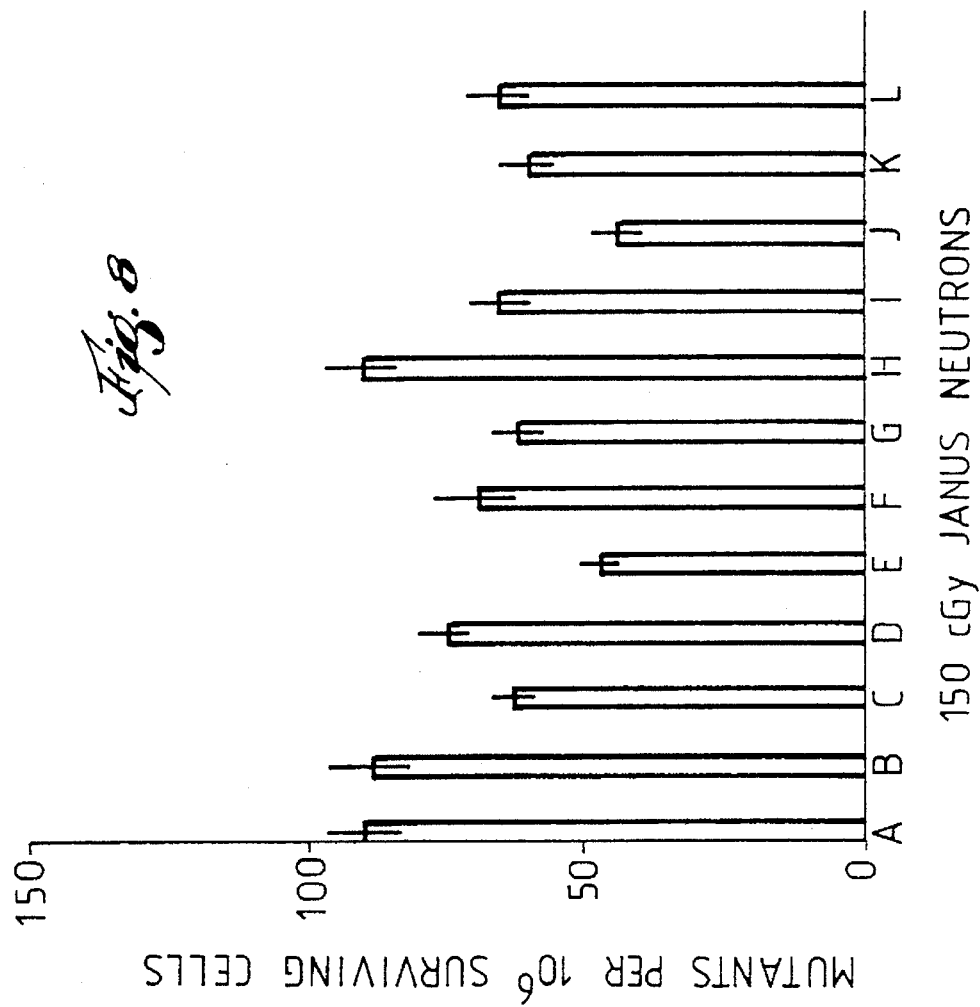

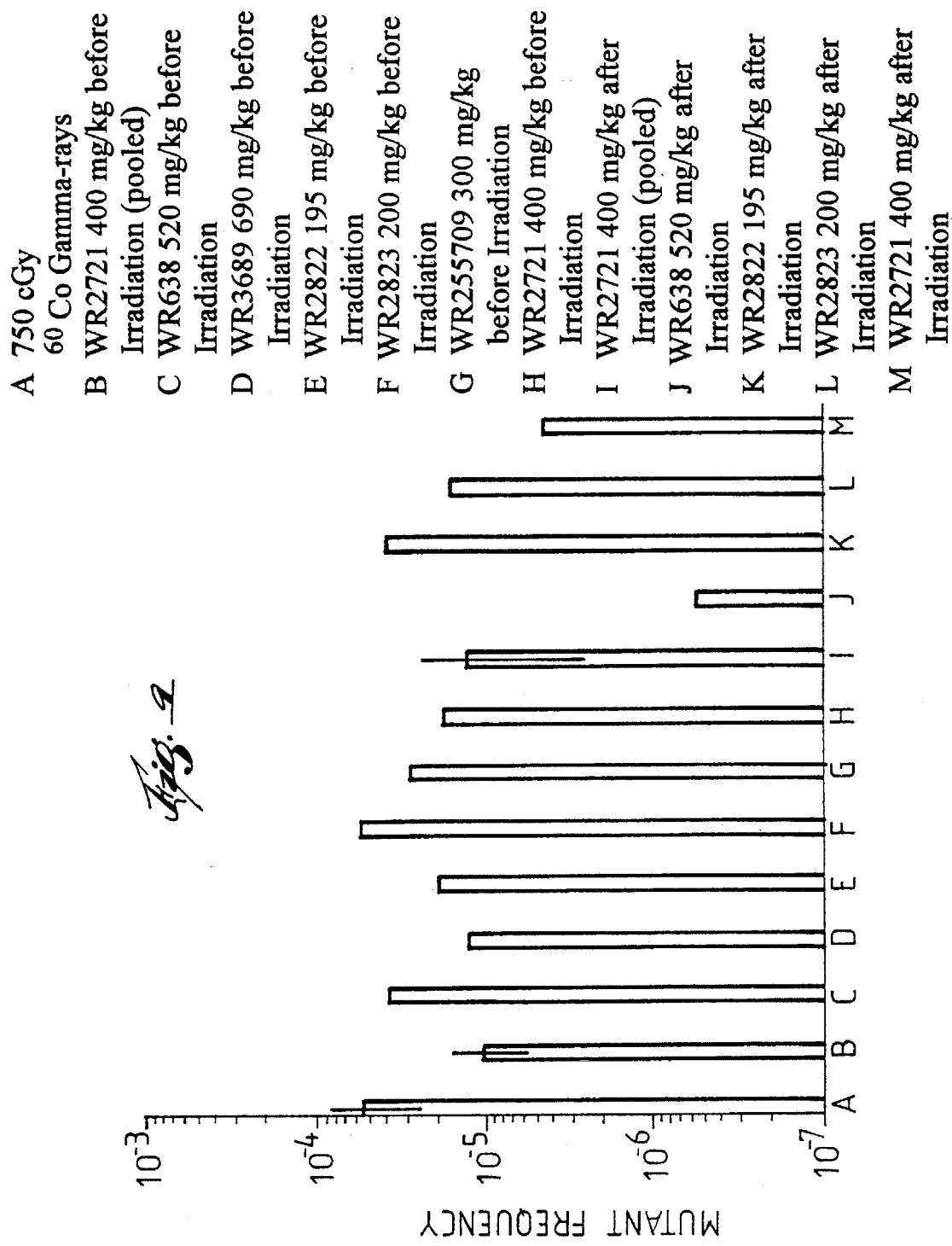

METHOD FOR PROTECTION AGAINST GENOTOXIC MUTAGENESIS

This invention was made with Government support under Contract No. W-31-109-ENG-38 awarded by the Department of Energy. The Government has certain rights in this invention.

Prior art techniques for protecting against the genotoxic effects of radiation by the S-omega-(omega-aminoalkylamino) alkyl dihydrogen phosphorothioates have focused on the pre-irradiation effect of dosages on amelioration of radiation's lethal effects with no appreciation for the anti-mutagenic, but only mutagenic effects. In prior art uses, it was required to administer maximum tolerated levels of the drugs prior to radiation exposure. Such requirements have limited the effectiveness of these agents because, when administered at the required maximum tolerated dose, they are debilitating causing fever, chills, rash, hypotension, nausea and vomiting. It is conventionally accepted that the drugs must be administered prior to radiation exposure which heretofore has precluded their use for individuals accidently exposed to radiation. Since 1949, the status of the prior art dictates that, in order for the radioprotective drug to be effective, it must be present before radiation exposure. The conventional understanding is also that the disulfide form of radioprotectors is incapable of providing protection. In drugs such as WR-2721 the level of protection is proportional to the amount of the drug administered. The prior art also teaches there are potential mutational properties of these agents which must be avoided. In particular, it has been suggested that one such agent in this class of phosphorothioates identified as S-2(3-aminopropylamino) ethyl phosphorothioic acid (also known as "WR-2721"), by way of intracellular reactions, can lead to the conversion of cytosine moieties in DNA to uracil. The result of use of WR-2721 can then be a mutagenic reaction in normal tissue.

These above enumerated concerns, along with conventional wisdom existing since as long ago as 1949, have prevailed and have discouraged investigation into the potential of phosphorothioates and related aminothiol compounds as chemopreventative agents.

These chemical agents are operationally defined as materials which can protect against genotoxic damage induced by known mutagens and carcinogens occurring as a result of ionizing radiation administered after injestion of the chemical agent or drugs. The accepted protective mechanisms of action of these drugs include: the scavenging of free radicals produced as a result of the radiolysis of cellular water (presumably, free radical damage to DNA); the repair of chemical lesions via hydrogen atom donation; and the induction of cellular hypoxia. The deleterious effects of radiation occur via the deposition of energy in less than $10^{-12}$ sec, while the relaxation of ionizations and excitations occur in less than $10^{-2}$ sec. Damage to DNA, which leads to cell lethality, is completed between $10^{-7}$ and $10^{-3}$ sec. These models are consistent with the failure to demonstrate protection against cell lethality by the phosphorothioates and related aminothiols when they are administered immediately following radiation exposure.

In 1985 it was reported that a free thiol designated 2-[(aminopropyl)amino] ethanethiol could protect against somatic mutations at the hypoxanthine-guanine phosphoribosyl transferase locus in cultured rodent cells (designated V79), even if it were administered 3 h following irradiation. These in vitro results relating to post irradiation exposure and protection by this agent against mutagenesis were extended in 1989 to include protection against fission-spectrum neutrons. The extreme toxicity of this agent precluded its testing under in vivo conditions to ascertain the actual anti-mutagenic effect in a mammal. In 1987 the drug cysteamine was tested as an antimutagen, but no protective effects were observed unless it was present during irradiation (administered prior to).

The problem of radiation-induced genotoxic damage leading to mutagenicity exists from both naturally occurring and man-made radiation sources. These range from cosmic radiations, ultra violet rays, radiations from nuclear reactors and war released materials, and radiations from diagnostic and therapeutic sources. The development of mutations and cancers arising from these radiations are well documented and prove to be a major health risk to the population as a whole as well as to high-risk groups employed in the nuclear power industry, military, and patients receiving diagnostic and therapeutic radiation treatments.

Accordingly, there exists a need for a method for protecting against radiation-induced mutations which will be amenable to pre- and/or post-radiation administration and which will be effective at relatively low non-toxic concentrations so as to allow use in mammals and also allow for multiple, as well as single, administrations.

Accordingly, it is an object of the present invention to provide a novel method and substance for reducing mutations of mammal cells, including humans, exposed to radiation.

It is another object of the invention to provide an improved method and aminothiol agents which diminish mutation of cells exposed to radiation, even though administered after irradiation.

It is an additional object of the invention to provide a method using S-omega-(omega-aminoalkylamino) alkyl dihydrogen phosphorothioates to mimimize the effects of irradiation on cell mutation.

It is still another object of the invention to provide a class of aminothiol agents which metabolize in vivo to produce free sulfhydryl groups and disulfides for protection against radiation-induced mutations in mammals.

It is a further object of the invention to provide a novel mechanism by which the resultant disulfide species found via the metabolic process of the phosphorothioate agent is utilized to diminish all mutations caused by irradiation.

These and other objects of the present invention will become apparent from consideration of the following description of preferred embodiments, examples, claims and the drawings described below.

BRIEF DESCRIPTION OF THE DRAWINGS

FIG. 6 demonstrates the behavior of the disulfide form (designated WR-33278) of 2-[(aminopropyl) amino] ethanethiol (designated WR-1065) compared to the polyamine spermine;

FIG. 8 demonstrates the effectiveness under in vitro conditions of 3-[(2-mercaptoethyl) amino] propionamide p-toluenesulfonate (designated WR-2529); S-1-(aminoethyl) phosphorothioic acid (designated WR-638); S-[2-(3-methylaminopropyl amino ethyl] phosphorothioate (designated WR-3689), S-1-(2hydroxy-3-amino) propyl phosphorothioic acid (WR-77913); and 2-[3-methylamino) propylamino] ethanethiol (designated WR-255592) in protecting against radiation-induced mutagenesis. These results are shown as a function of administration either 30 min before or immediately after irradiation with 150 cGy of fission-spectrum neutrons. Each error bar is one standard error of the mean; and FIG. 9 demonstrates the effectivess, under in vivo conditions, of S-2-(3-aminopropylamino) ethyl phosphorothioic acid (WR-2721); S-1-(aminoethyl) phosphorothioic acid (WR-638); S-[2-(3-methylaminopropyl) aminoethyl] phosphorothioate acid (WR-3689); S-2-(4-aminobutylamino) ethylphosphorothioic acid (WR-2822); S-2-(5-aminopentylamino) ethyl phosphorothioic aid (WR-2823); 1-[3-(3-aminopropyl) thiazolidin-2-Y1]-D-gluco-1,2,3,4,5-pentane-pentol dihydrochloride (WR-255709), in protecting against radiation-induced mutagenesis as a function of administration either 30 min before or immediately after irradiation of B6CF, mice with 150 cGy of fission-spectrum neutrons.

DESCRIPTION OF THE PREFERRED EMBODIMENTS

The present invention is concerned with four general areas: (1) chemicals of the phosphorothioate designation and associated metabolites, when administered to mammals (i.e., mice) following mutagen exposure (i.e., ionizing radiation including photon and fission-spectrum neutrons),protect against genotoxic damage which normally leads to the development of somatic mutations; (2) protection is obtained against mutagen-induced mutations by the phosphorothioates and associated metabolites at very low concentrations which are much less than required for protection against cell lethality; (3) protection against mutagen-induced somatic mutations by the phosphorothioates and associated metabolites is shown to correlate most closely with the disulfide metabolite; and (4) the ability to protect against mutagen-induced somatic mutations is a general property of the genus of phosphorothioates and their associated metabolites; and this is demonstrated by the observed antimutagenic properties of the species S-1-(aminoethyl) phosphorothioic acid (WR-638), S-[2-(3-methylaminopropyl) aminoethyl] phosphorothioate (WR-3689), S-2-(4-aminobutylamino) ethylphosphorothioic acid (WR-2822), 3-[(2-mercapto ethyl) amino] propionamide p-toluenesulfonate (WR-2529), S-1-(2-hydroxy-3-amino) propyl phosphorothioic acid (WR-77913), 2-[3-(methylamino) propylamino] ethanethiol WR-255591), S-2-(5-aminopentylamino) ethyl phosphorothioic acid (WR-2823), and 1-[3-(3-aminopropyl) thiazolidin-2-Y1]-D-gluco-1,2,3,4,5 pentane-pentol dihydrochloride (WR-255709).

I. Phosphorothioate Genus Protection After Irradiation

Figure 1:
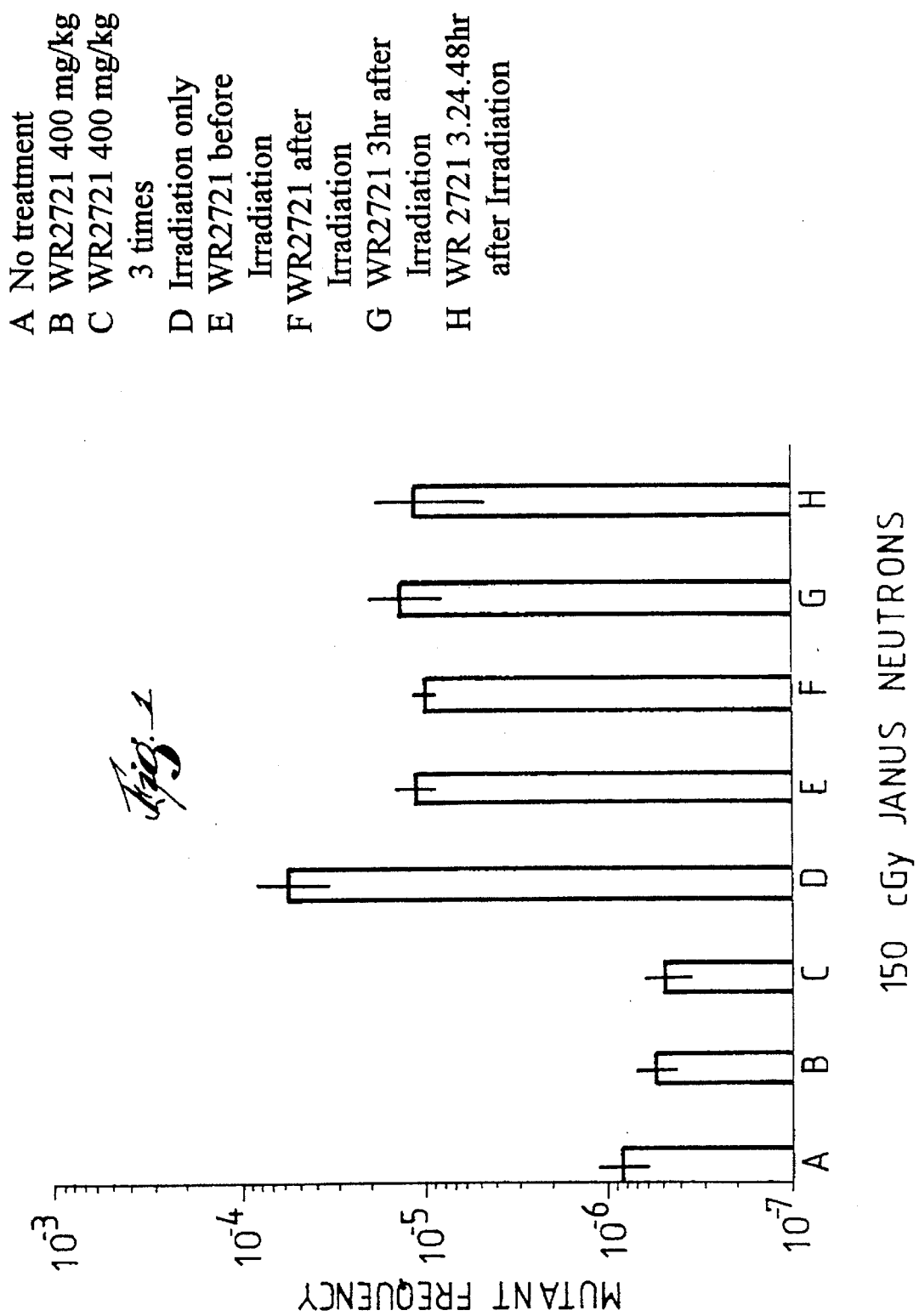
FIG. 1 demonstrates the performance of S-2-(3-aminopropylamino) ethylphosphorothioic acid (also identified as WR-2721) to protect against radiation-induced mutagenesis when administered either 30 min before, immediately after, or 3 h following irradiation. Error bars represent one standard error of the mean.

Chemicals of the phosphorothioate genus and associated metabolites can protect against somatic mutations when administered to mammals following a mutagen exposure. This conclusion is based on the observation that S-2-(3-aminopropylamino) ethyl phosphorothioic acid, administered at a dose of 400 mg/kg up to 3 h following neutron radiation exposure, affords substantial protection against radiation-induced mutations at the hypoxanthine-guanine phosphoribosyl transferase locus in the T lymphocytes of mice (see FIG. 1, ref. 10). The magnitude of protection is unchanged regardless of whether the phosphorothioate was administered 30 min before, immediately following (i.e, within 10 min), or up to 3 h following irradiation of the test animals.

The spontaneous mutant frequency of T lymphocytes from unirradiated control animals was stable and ranged from $9-10 \times 10^{-7}$. Following irradiation with 150 cGy of fission neutrons, the mutant frequency increased to $5.6 \times 10^{-5} \pm 2.3 \times 10^{-5}$ (1 standard error of the mean). Mutant frequencies in animals administered S-2-(3-aminopropylamino) ethylphosphorothioic acid 30 min before immediately after, or 3 h following irradiation with 150 cGy of fission neutrons were $1.1 \times 10^{-5} \pm 2.6 \times 10^{-6}$, $1.0 \times 10^{-5} \pm 1.3 \times 10^{-6}$ and $1.4 \times 10^{-5} \pm 5.8 \times 10^{-6}$, respectively.

II. Phosphorothioate Protection from Low Dosages

Figure 2:
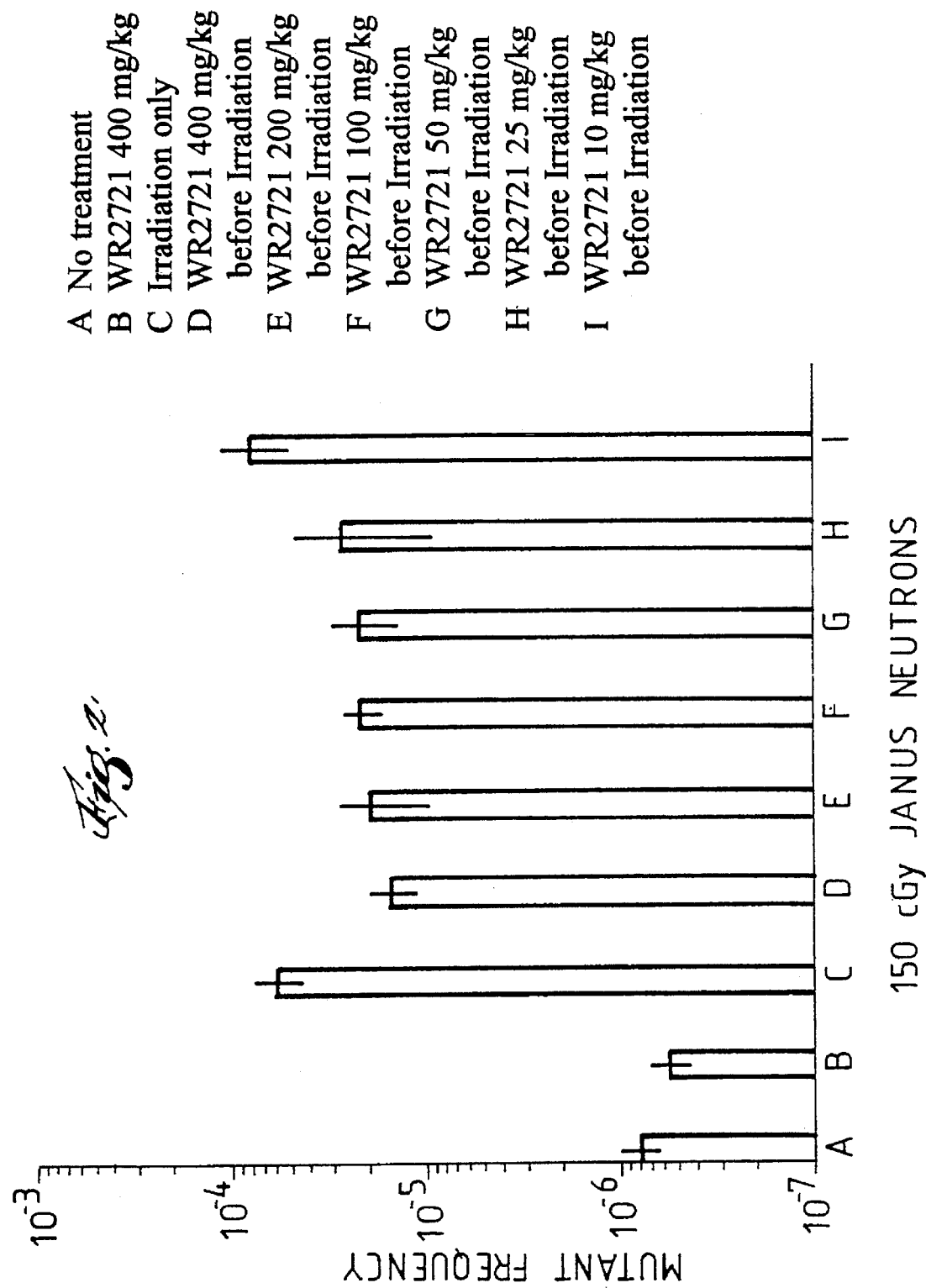
FIG. 2 demonstrates the performance at low concentrations of S-2-(3-aminopropylamino) ethylphosphorothioic acid (i.e., WR-2721) in the range of from 400 mg/kg to 10 mg/kg. Error bars represent one standard error of the mean.
Figure 3:
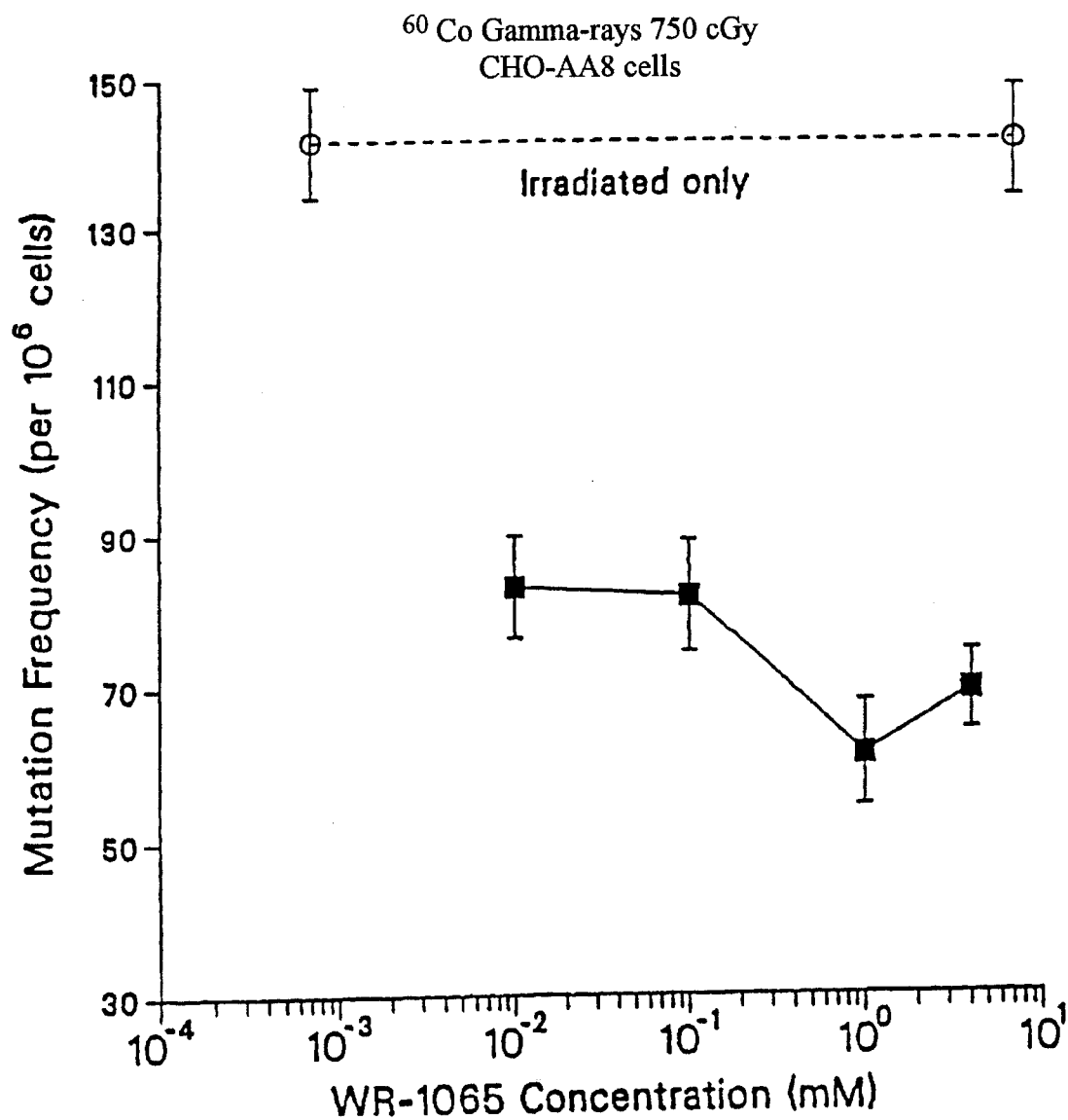
FIG. 3 demonstrates the relationship between the concentration of 2-[(aminopropyl) amino] ethanethiol (i.e., WR-1065) and its protective ability against radiation-induced mutagenesis. Each error bar is one standard error of the mean.

The phosphorothioates and associated metabolites further achieve mutagen protection at very low concentrations, compared to concentrations required to protect against cell lethality. This conclusion is based on the observations that S-2-(3-aminopropylamino) ethyl phosphorothioic acid is equally antimutagenic at concentrations of 400 mg/kg, 200 mg/kg, 100 mg/kg, and 50 mg/kg (see FIG. 2, ref. 10). Mutant frequencies of T lymphocytes isolated from mice irradiated with 150 cGy of fission neutrons were $9.0 \times 10^{-5} \pm 1.2 \times 10^{-5}$ (1 standard error of the mean) for irradiated controls, $1.2 \times 10^{-5} \pm 1.0 \times 10^{-5}$ (S.E.) for 400 mg/kg, $7.8 \times 10^{-6} \pm 2.7 \times 10^{-6}$ (S.E.) for 200 mg/kg, $1.5 \times 10^{-5} \pm 1.4 \times 10^{-6}$ (S.E.) for 100 mg/kg, and $6.3 \times 10^{-6} \pm 3.2 \times 10^{-6}$ (S.E.) for 50 mg/kg. Under in vitro conditions, the free thiol form of S-2-(3-aminopropylamino) ethylphosphorothioic acid, i.e., 2-[(aminopropyl) amino] ethanethiol was administered as an antimutagen to cultured Chinese hamster ovary cells at a concentration range from 4 mM down to 0.01 mM. When administered 30 min prior to irradiation with 750 cGy of $^{60}$Co gamma rays (see FIG. 3), the drug and its metabolite is significantly effective as an antimutagen.

Figure 4:
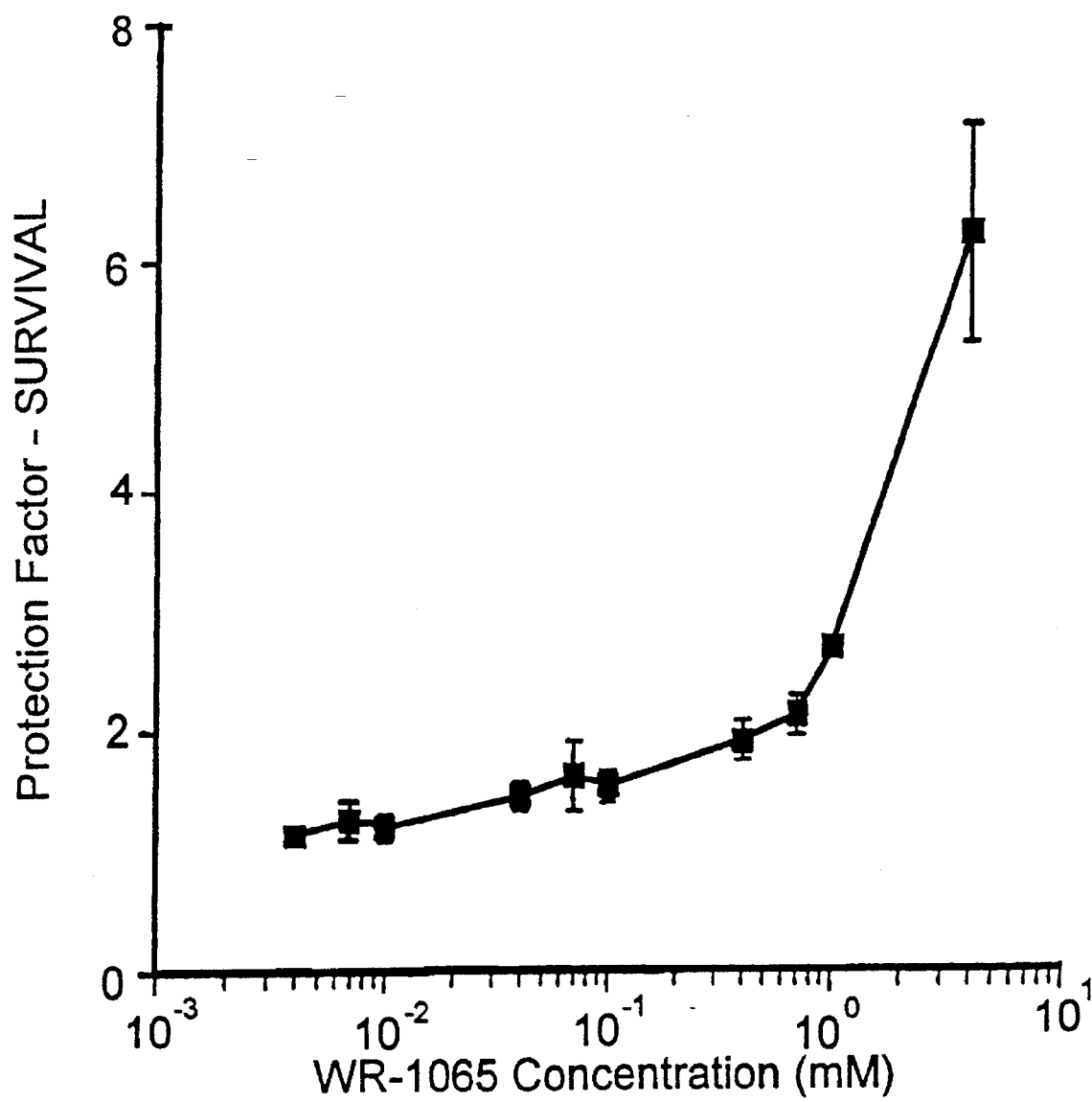
FIG. 4 demonstrates the effect of concentration of 2-[(aminopropyl) amino] ethanethiol (i.e., WR-1065) on its protective ability against radiation-induced lethality. Each error bar is one standard error of the mean.

Administration of 2-[(aminopropyl) amino] ethanethiol also results in the formation of its disulfide. Protection against the cell killing effects of radiation by 2-[(aminopropyl) amino] ethanethiol rapidly diminishes as the concentration falls from 4 mM to 0.01 mM (see FIG. 4).

III. Disulfide Metabolite Mutagenic Protection

Figure 5A:
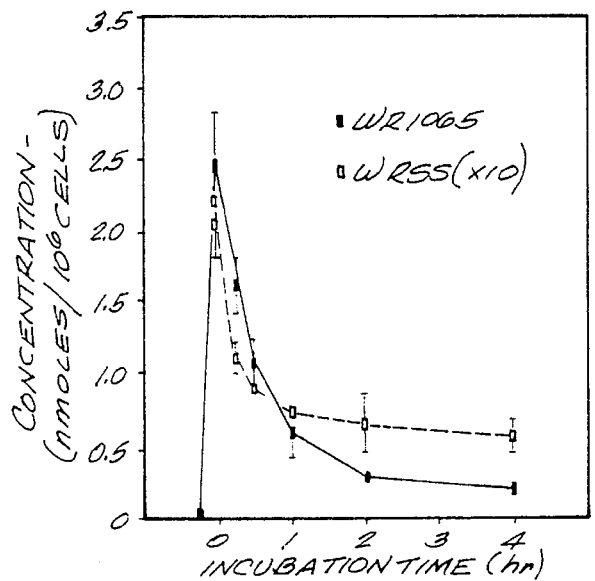
FIG. 5 demonstrates the effect of cellular levels of 2-[(aminopropyl) amino] ethanethiol (i.e., WR-1065) and its disulfide (i.e., WRSS) on the protection against cell killing in FIG. 5B and protection against mutagenesis in FIG. 5C following irradiation with 150 cGy of fission-spectrum neutrons. Each error bar is one standard error of the mean.
Figure 5B:
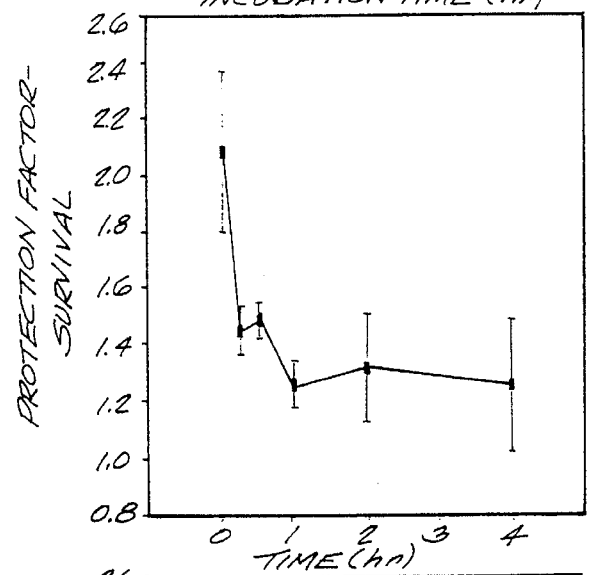
Figure 5C:
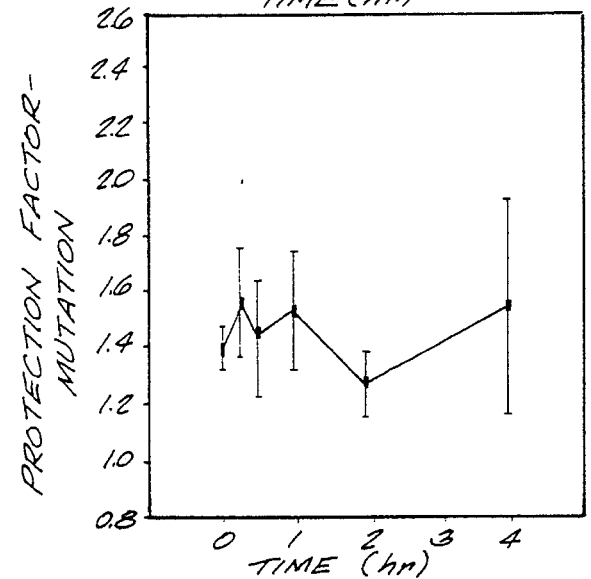
Figure 7B:
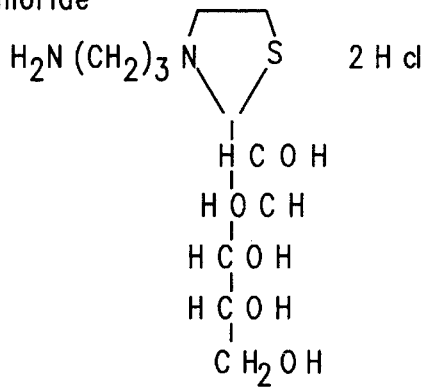
FIG. 7i and ii illustrates the chemical structures of the phosphorothioates/aminothiols used.

The presence of disulfide metabolite of the phosphorothioate class of compounds corresponds to antimutagenic protection. This conclusion is based on the observations that, following the administration of 4 mM of 2-[(aminopropyl) amino] ethanethiol, protection against radiation-induced (i.e., fission neutrons) somatic mutations at the hypoxanthine-guanine phosphoribosyl transferase locus in Chinese hamster ovary cells correlates with the measured disulfide as compared to the free thiol (see FIG. 5).

Subsequent thiol and disulfide concentrations were measured by using monobromobiamine (mBBr), which reacts selectively with thiols via a Sn 2 displacement process to produce a fluorescent derivative. These methods were developed to specifically measure 2-[(aminopropyl) amino] ethanethiol, its phosphorothioate, and its disulfide. Chinese hamster ovary cells, $5 \times 10^6$ in 5 ml of growth medium, were administered 4 mM of 2-[(aminopropyl) amino] ethanethiol for 30 min at 37° C. They were then centrifuged, washed with a buffer, and resuspended in fresh medium up to an additional 4 h. After 15 min, 30 min, 1 h, 2h, and 4 h of incubation, a sample of cells was removed and exposed to 150 cGy of fission neutrons. At these times various measurements made included: survival measurements, mutation measurements, and intracelluar measurements of 2-[(aminopropyl) amino] ethanethiol and its disulfide. The data contained in FIG. 5 demonstrate that survival protection is well correlated with thiol measurements. This is consistent with conventional understandings and teachings. The disulfide concentration was measured to be significantly less than that of the thiol, but the rate of its decrease with time was less than that found for the thiol. Measured protection against mutagenesis remained constant over this time range correlating with the kinetics of disulfide as opposed to the thiol concentration. The disulfide form of this thiol closely resembles the polyamine spermine (see FIG. 6). Polyamines are known to be involved in the repair of DNA damage due to ionizing and UV irradiation. The measurements indicate an inability to protect against radiation-induced lethality by the phosphorothioate class of chemicals and their associated metabolites when they are added after radiation. Coupling these data with the demonstrated ability to protect against radiation-induced mutagenesis under similar post radiation exposure conditions, make it clear that it is thus the fidelity, not the amount or quantity, of DNA damage which is being affected by these agents. This is also consistent with the properties of polyamines which have been shown to stabilize DNA against enzymatic degradation. The prior art has indicated that the disulfide is not a protective metabolite of either the phosphorothioates or thiols. The instant data indicates however that the disulfide metabolite of the phosphorothioate is a protective moiety in preventing mutagen- (i.e., radiation) induced somatic mutations. The disulfide metabolite has a close similarity in structure and composition to polyamines, which are known endogenous agents capable of stabilizing chromatin and affecting DNA repair. Further, the phosphorothioates S-2-(3-aminopropylamino) ethyl (WR-2721), S-2-(4-aminobutylamino) ethyl (WR-2822), and S-2-(7-aminoheptylamino) ethyl have been shown in the prior art to competitively inhibit the uptake of the polyamine putrescine into rat lung tissue. The importance of the disulfide moiety in the post mutagen (i.e., radiation) exposure-protection process against the formation of somatic mutations demonstrates a surprising advantage for phosphorothioate compounds which form polyamine-like disulfides for use as antimutagenic chemopreventive agents. IV. Phosphorothioate Protection Against Mutagenesis The ability to protect against mutagen-induced somatic mutations is a general property of the phosphorothioates and their associated metabolites. This advantage demonstrated by the data obtained by experiments on cultured Chinese hamster ovary cells first exposed to 150 cGy of fission neutrons and then applying for 30 min a quantity of 4 mM of either 3-[(2-mercaptoethyl) amino] propionamide p-toluenesulfonate (WR-2529), S-1-(aminoethyl) phosphorothioic acid (WR-638), S-[2-(3-methylaminopropyl) aminoethyl] phosphorothioate acid (WR-3689), and S-1-(2-hydroxy-3-amino) propyl phosphorothioic acid (WR-77913) (see FIG. 8). All of these agents, including 2-[3-(methylamino) propylamino] ethanethiol (WR-255591) were effective antimutagens when they were added to cells at a concentration of 4 mM at about 30 min prior to exposure to fission neutrons (see FIG. 8).

Protection against radiation-induced somatic mutations in mammals (i.e., mice) was also demonstrated for S-1-(aminoethyl) phosphorothioic acid (WR-638) under conditions in which a dose of 520 mg/kg was administered ip to animals within about 10 min after whole-body exposure to 750 cGy of $^{60}$Co gamma rays (see FIG. 9). Phosphorothioates exhibited antimutagenic properties in mammals when administered 30 min prior to exposure to 750 cGy of $^{60}$Co gamma rays. The phosphorothioates included S-[2-(3-methylaminopropyl) aminoethyl] phosphorothioate acid (WR-3689), and S-2-(4-aminobutylamino) ethylphosphorothioic acid (WR-2822). These data demonstrate that the antimutagenic properties of S-2-(3-aminopropylamino) ethylphosphorothioic acid (WR-2721) are also observable in selected ones of the phosphorothioates and their associated metabolites.

While preferred embodiments of the invention have been shown and described, it will be clear to those skilled in the art that various changes and modifications can be made without departing from the invention in its broader aspects as set forth in the claims provided hereinafter.

What is claimed is:

1. A method for reducing mammal cell mutations induced by prior irradiation, comprising the step of:

(a) preparing a dosage of at least about 25 mg/kg of mammal body weight of a chemical compound selected from the group consisting of an aminoalkylphosphorothioate and an associated aminoalkylphosphorothioate metabolite; and (b) administering said dosage to the mammal up to about 3 hours after irradiation of the mammal.

2. The method as defined in claim 1 wherein said dosage is about 25–400 mg/kg mammal weight.

3. The method as defined in claim 1 wherein said phosphorothioate and metabolite is selected from the group consisting of S-1-(aminoethyl) phosphorothioic acid (WR-638), S-[2-(3-methylaminopropyl) aminoethyl] phosphorothioate acid (WR-3689), S-2-(4-aminobutylamino) ethylphosphorothioic acid (WR-2822), 3-[(2-mercapto ethyl) amino] propionamide p-toluenesulfonate (WR-2529), S-1-(2-hydroxy-3-amino) propyl phosphorothioic acid (WR-77913), 2-[3-(methylamino) propylamino] ethanethiol (WR-255591), S-2-(5-aminopentylamino) ethyl phosphorothioic acid (WR-2823), and 1-[3-(3-aminopropyl) thiazolidin-2-Y1]-D-gluco-1,2,3,4,5 pentane-pentol dihydrochloride (WR-255709).

4. The method as defined in claim 1 wherein the irradiation is fast neutrons.

* * * * *